United States Patent
Chang et al.

(10) Patent No.: US 12,404,255 B2
(45) Date of Patent: Sep. 2, 2025

(54) COMPOUND AND PHARMACEUTICAL COMPOSITION CONTAINING SAME FOR TREATING OR PREVENTING NEURAL DAMAGE, NEURAL DISEASE, OR DEVELOPMENTAL DISORDER THROUGH PROMOTING PROLIFERATION, DIFFERENTIATION, AND/OR REGENERATION OF NEURAL CELLS

(71) Applicants: ETNOVA THERAPEUTICS CORP., Seongnam-si (KR); KYUNGPOOK NATIONAL UNIVERSITY INDUSTRY-ACADEMIC COOPERATION FOUNDATION, Daegu (KR)

(72) Inventors: Sha Joung Chang, Seongnam-si (KR); Yeoun Hee Kim, Daegu (KR); Jung Jin Lee, Daegu (KR); Ga Ram Choi, Daegu (KR); Yong Min Chang, Daegu (KR)

(73) Assignees: ETNOVA THERAPEUTICS CORP, Seongnam (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 503 days.

(21) Appl. No.: 17/999,337

(22) PCT Filed: Aug. 25, 2020

(86) PCT No.: PCT/KR2020/011305
§ 371 (c)(1),
(2) Date: Nov. 18, 2022

(87) PCT Pub. No.: WO2021/251551
PCT Pub. Date: Dec. 16, 2021

(65) Prior Publication Data
US 2023/0183192 A1   Jun. 15, 2023

(30) Foreign Application Priority Data
Jun. 12, 2020   (KR) ........................ 10-2020-0071638

(51) Int. Cl.
C07D 257/02   (2006.01)

(52) U.S. Cl.
CPC .................................. C07D 257/02 (2013.01)

(58) Field of Classification Search
CPC ..................................................... C07D 257/02
USPC ......................................................... 514/563
See application file for complete search history.

(56) References Cited

U.S. PATENT DOCUMENTS
2010/0322855 A1   12/2010   Chong

FOREIGN PATENT DOCUMENTS
JP   2012504131   2/2012
KR   20180081558   7/2018

OTHER PUBLICATIONS

Crich et al., "In Vitro and in Vivo Magnetic Resonance Detection of Tumor Cells by Targeting Glutamine Transporters with Gd-Based Probes." J. Med. Chem. 2006, vol. 49, pp. 4926-4936.
International Search Report and Written Opinion issued in Corresponding PCT Application No. PCT/KR2020/011305, dated Mar. 11, 2021.
Lee et al., "All-Trans-Retinoic Acid as a Novel Therapeutic Strategy for Alzheimer's Disease" Expert Rev Neurother. 2009, 9(11), pp. 1615-1621.

*Primary Examiner* — Kristin A Vajda
(74) *Attorney, Agent, or Firm* — NORTON ROSE FULBRIGHT US LLP

(57) ABSTRACT

The present invention relates to a compound of formula 1 and a pharmaceutical composition containing same. This compound may be useful as: a therapeutic agent for degenerative brain diseases including dementia or cranial nerve diseases and developmental disorders caused by neural cell damage, various degenerative neural diseases, ischemic nerve diseases, or neural damage diseases; a learning ability-improving agent; and a cognitive function-improving agent. [Formula 1] in formula 1 above, B represents a part derived from retinoic acid.

7 Claims, 12 Drawing Sheets

COMPOUND AND PHARMACEUTICAL COMPOSITION CONTAINING SAME FOR TREATING OR PREVENTING NEURAL DAMAGE, NEURAL DISEASE, OR DEVELOPMENTAL DISORDER THROUGH PROMOTING PROLIFERATION, DIFFERENTIATION, AND/OR REGENERATION OF NEURAL CELLS

CROSS-REFERENCE TO RELATED APPLICATIONS

This application is a national phase under 35 U.S.C. § 371 of International Application No. PCT/KR2020/011305, filed Aug. 25, 2020, which claims the benefit of priority to Korean Patent Application No. 10-2020-0071638, filed Jun. 12, 2020. The contents of each of the referenced applications are incorporated into the present application by reference in their entireties.

FIELD OF THE INVENTION

The present disclosure relates to a novel compound and a pharmaceutical composition for treatment or prevention of neuronal damage, neurological disease, or developmental disorder via promotion of proliferation, differentiation, and/or regeneration of nerve cells, the composition containing the compound.

DESCRIPTION OF RELATED ART

Nerve cells are distributed in numerous places in a body including a brain. The body may sense external situations, and think over the external situations, react therewith, and perform exercise in response thereto via transmission of signals between the nerve cells. Therefore, when the nerve cells die due to certain factors, various symptoms such as cognitive impairment symptoms, paralysis symptoms, sensory disturbance symptoms, and motor abnormalities may occur. Alzheimer's disease is caused due to death of nerve cells in the brain, which is responsible for memory. Parkinson's disease is caused due to death of nerve cells in a place in the body that control movement.

When the nerve cells die, it is very difficult to regenerate the nerve cells again. Although cells other than the nerve cell such as skin cells are destroyed by damage, and other cells around the damaged cells are divided to create new cells to replace the damaged cells. However, the nerve cell does not divide. Thus, it is very difficult to treat diseases associated with the death of the nerve cells. Accordingly, until now, treatment of many diseases caused by the death of the nerve cells is effective only in alleviating the symptoms. Thus, there is still a need to develop a substance that may effectively treat or prevent neuronal damage, neurological diseases, and developmental disorders via regeneration of the nerve cells.

SUMMARY OF THE INVENTION

One purpose of the present disclosure is to provide a novel compound capable of effectively treating or preventing neuronal damage, neurological disease, or developmental disorder, and a pharmaceutical composition containing the same.

The above purpose of the present disclosure may be achieved by providing a compound represented by a following Chemical Formula 1, and a pharmaceutical composition containing the same:

[Chemical Formula 1]

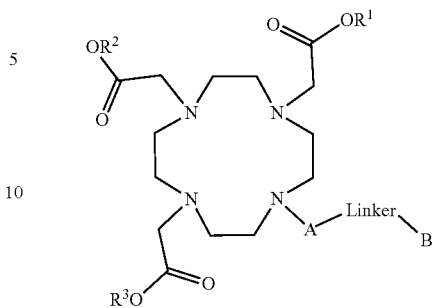

In the Chemical Formula 1,
each of $R_1$ to $R_3$ independently represents hydrogen, linear or branched (C1-C10)alkyl, or an electron pair to form any bond,
A represents $*\!-\!(CH_2)_n\!-\!A^1\!-\!*$,
n represents any integer from 0 to 5,
$A^1$ represents $*\!-\!COO\!-\!*$, $*\!-\!CO\!-\!*$, $*\!-\!NR^4\!-\!*$, $*\!-\!CH_2\!-\!*$, $*\!-\!CONH\!-\!*$, or $*\!-\!O\!-\!*$,
Linker represents $*\!-\!L^1\!-\!NHCO\!-\!L^2\!-\!*$, $*\!-\!L^1\!-\!O\!-\!R\!-\!O\!-\!L^2\!-\!*$, $*\!-\!L^1\!-\!CH_2\!-\!L^2\!-\!*$, $*\!-\!L^1\!-\!NR^5\!-\!L^2\!-\!*$, or $*\!-\!L^1\!-\!COO\!-\!L^2\!-\!*$,
$L^1$ represents linear or branched (C1-C30)alkyl,
$L^2$ represents a single bond or linear or branched (C1-C30)alkyl,
R represents linear or branched (C1-C20)alkyl,
each of $R^4$ and $R^5$ independently represents hydrogen or linear or branched (C1-C10)alkyl,
B represents a moiety derived from retinoic acid.

Until now, treatment of neuronal damage or neurodegeneration and various diseases related thereto has been effective only in alleviating disease progression, and there has been no treatment agent capable of completely treating the same. The compound according to the present disclosure may directly induce or promote generation of neurites, growth of neurites, differentiation of nerve cells, regeneration of nerve cells, and/or proliferation of nerve cells and thus may realize radical treatment of various neurological diseases. In addition, due to low cytotoxicity of the compound, the compound may be free of side effects due to drug toxicity. Further, due to high solubility of the compound in water and high dissolution stability thereof in water, formulation flexibility of a formulation containing the compound is high, and absorption thereof into the body is increased, so that nerve cell regeneration, differentiation, and protective effects may be further increased.

3B is a graph showing neuronal cytotoxicity based on a concentration of the MMB-11903B compound and an elapsed time.

Figure 4:
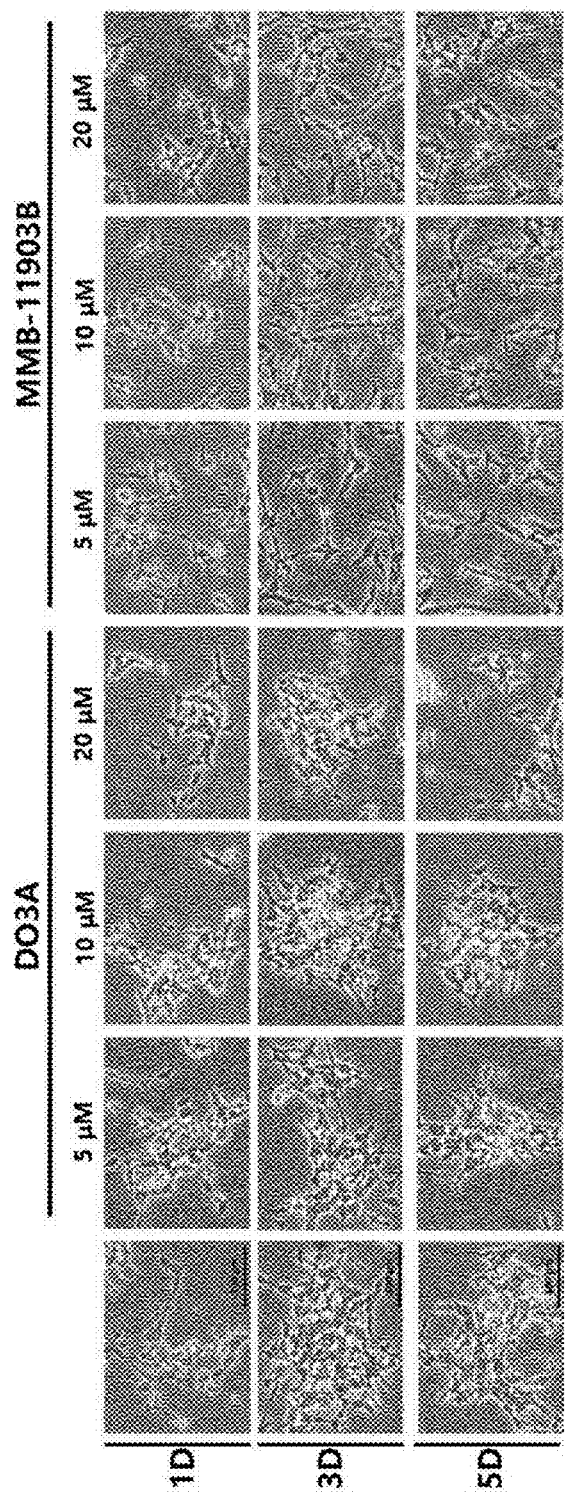

FIG. 4 is an image of a nerve cell morphology based on a concentration and a treatment time of each of DO3A and MMB-11903B compounds.

Figure 5A:
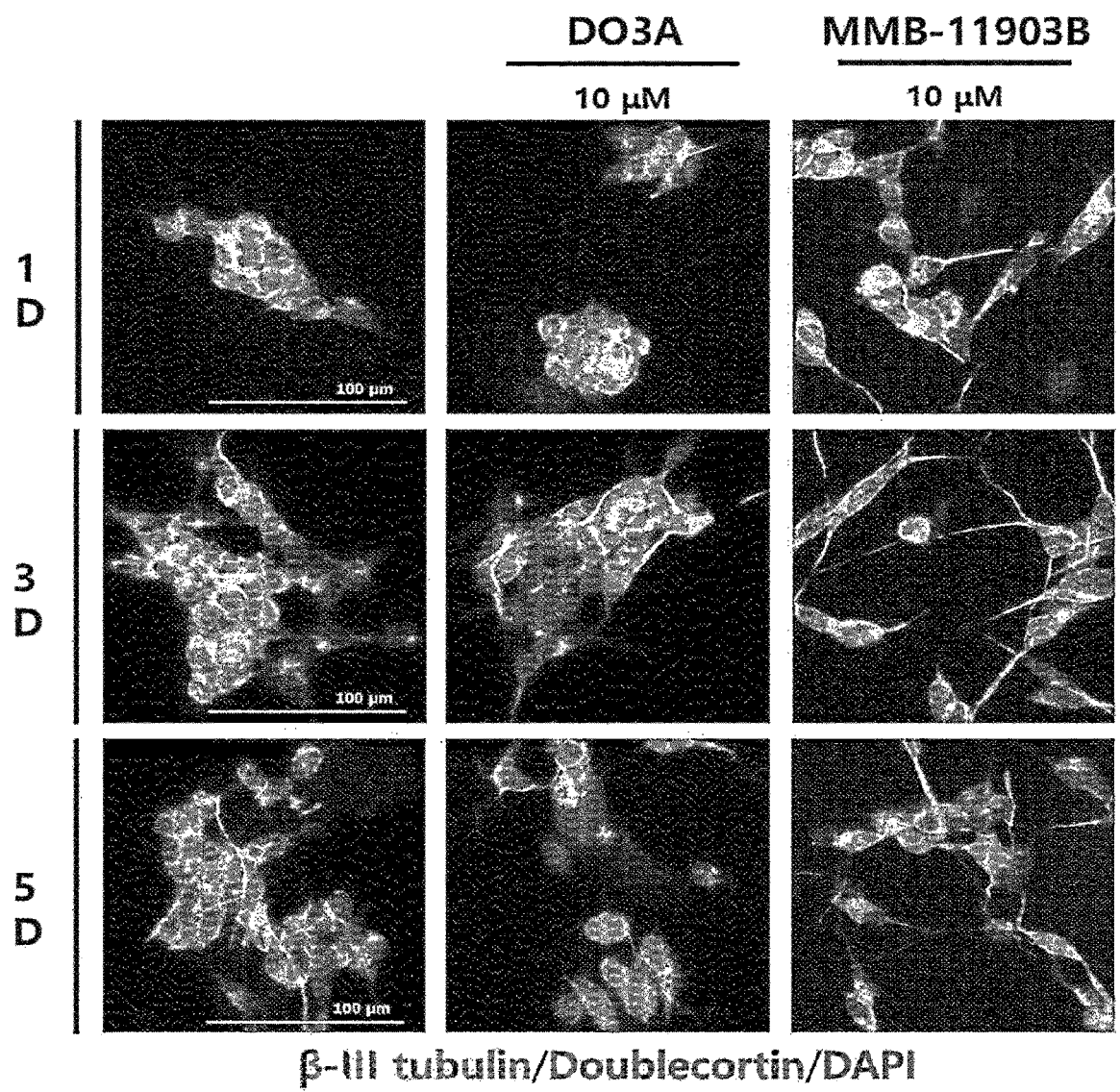
Figure 5B:
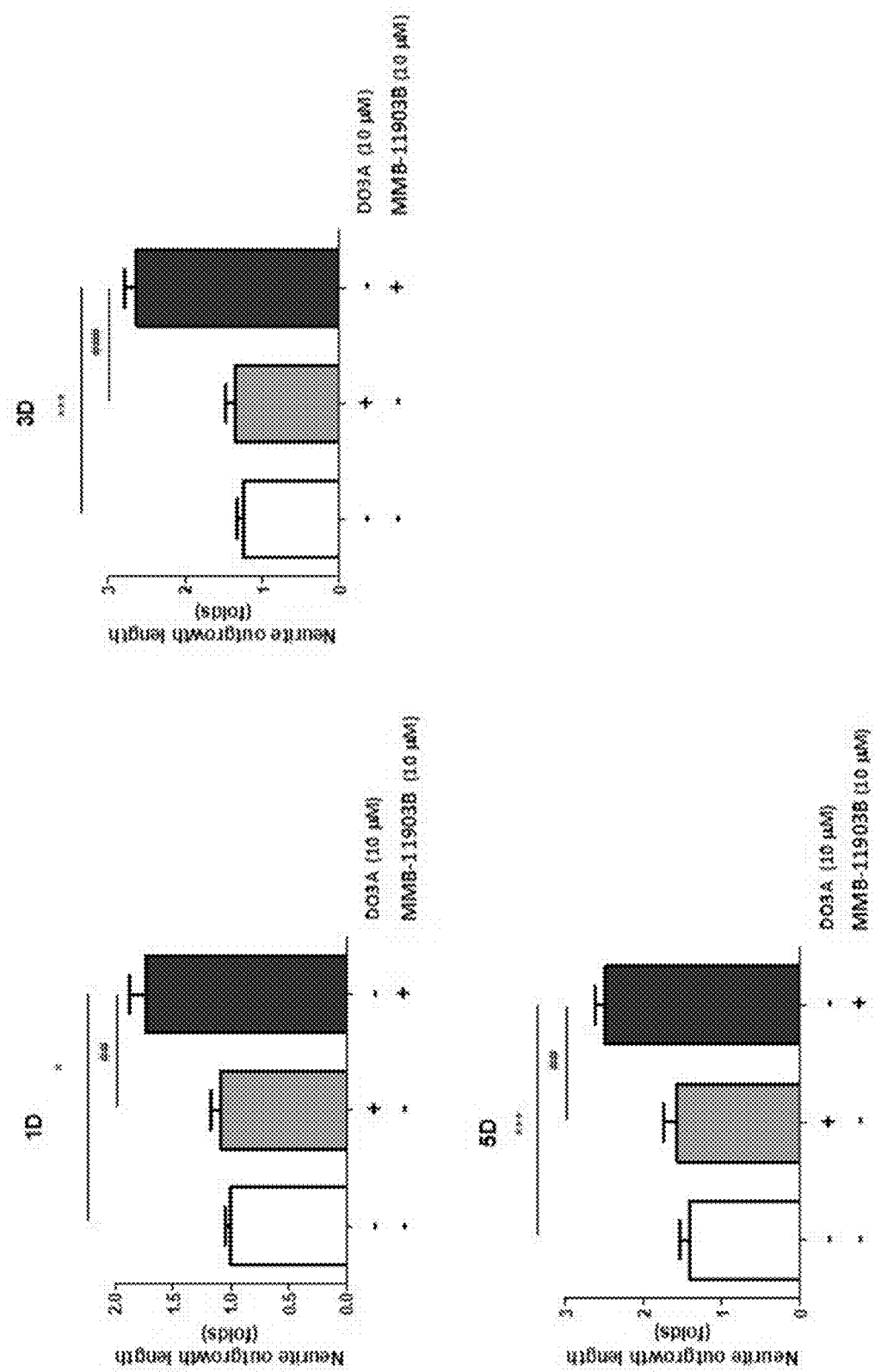

FIG. 5A is an image obtained using a fluorescence microscope after a nerve cell line treated with each of DO3A and MMB-11903B compounds is stained with a marker for neuronal differentiation. FIG. 5B is a graph showing a measurement of a neurite length of a nerve cell that is changed after treatment thereof with each of DO3A and MMB-11903B compounds.

Figure 6A:
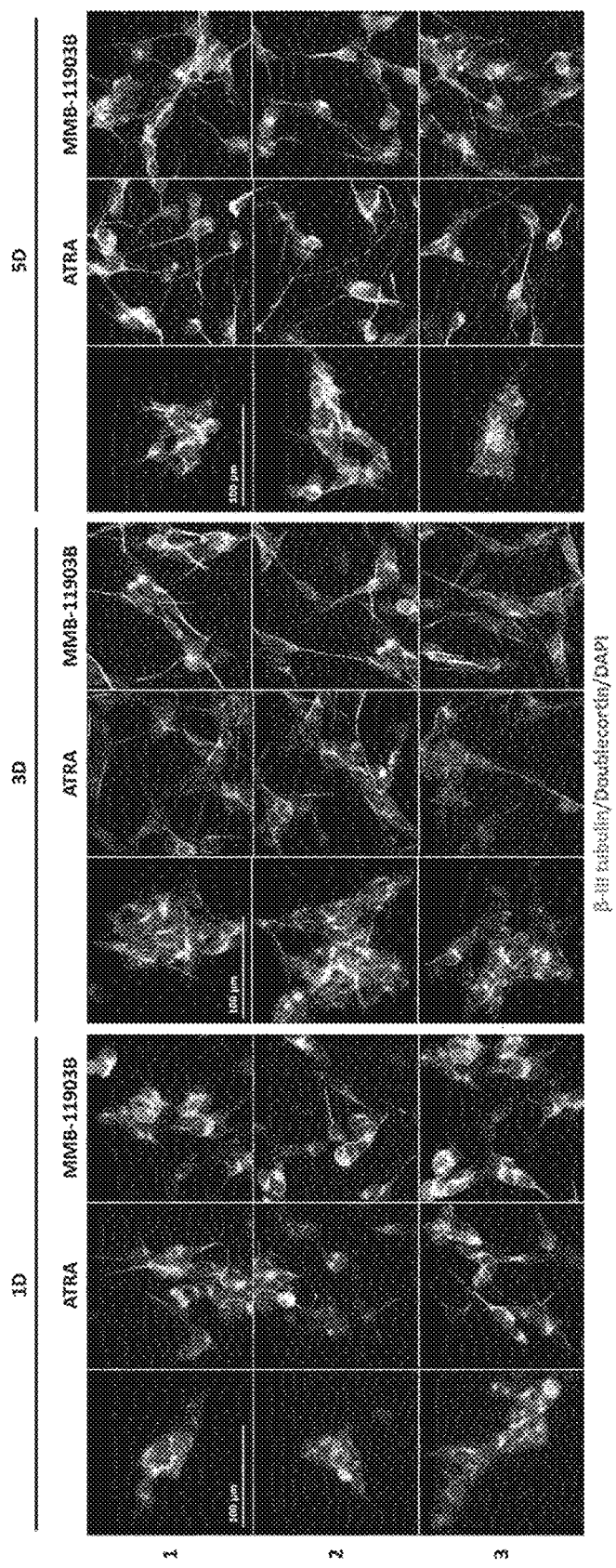
Figure 6B:
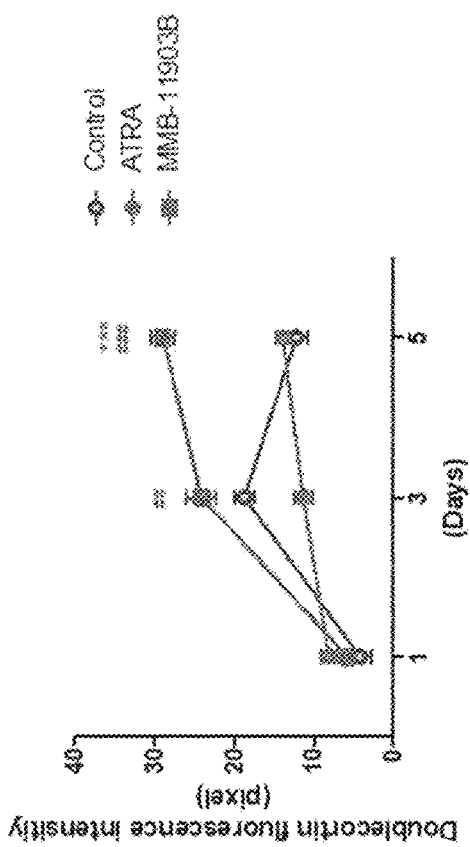
Figure 6B:
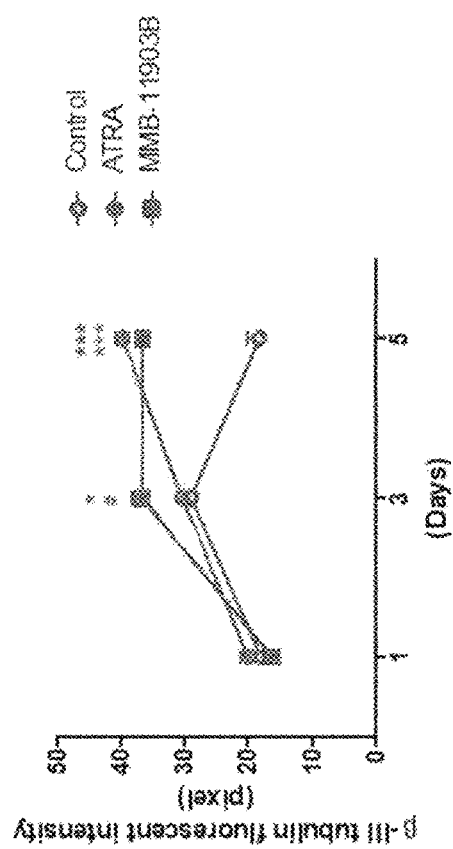

FIG. 6A is an image obtained using a fluorescence microscope after a nerve cell line treated with each of ATRA and MMB-11903B compounds is stained with a marker for neuronal differentiation. FIG. 6B is a graph of a color histogram of an expression level measured using an antibody of a marker for neuronal differentiation in order to examine differentiation of a nerve cell treated with each of ATRA and MMB-11903B according to the present disclosure.

Figure 7A:
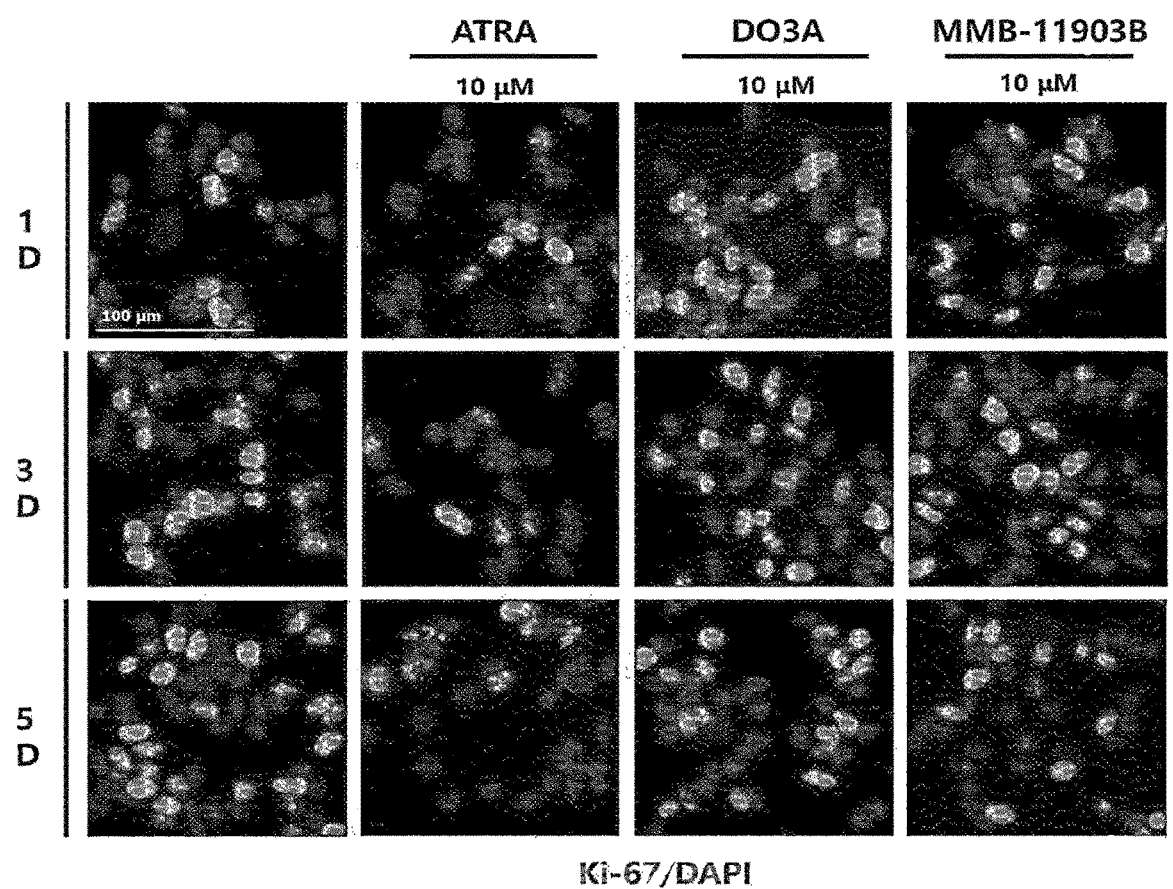
Figure 7B:
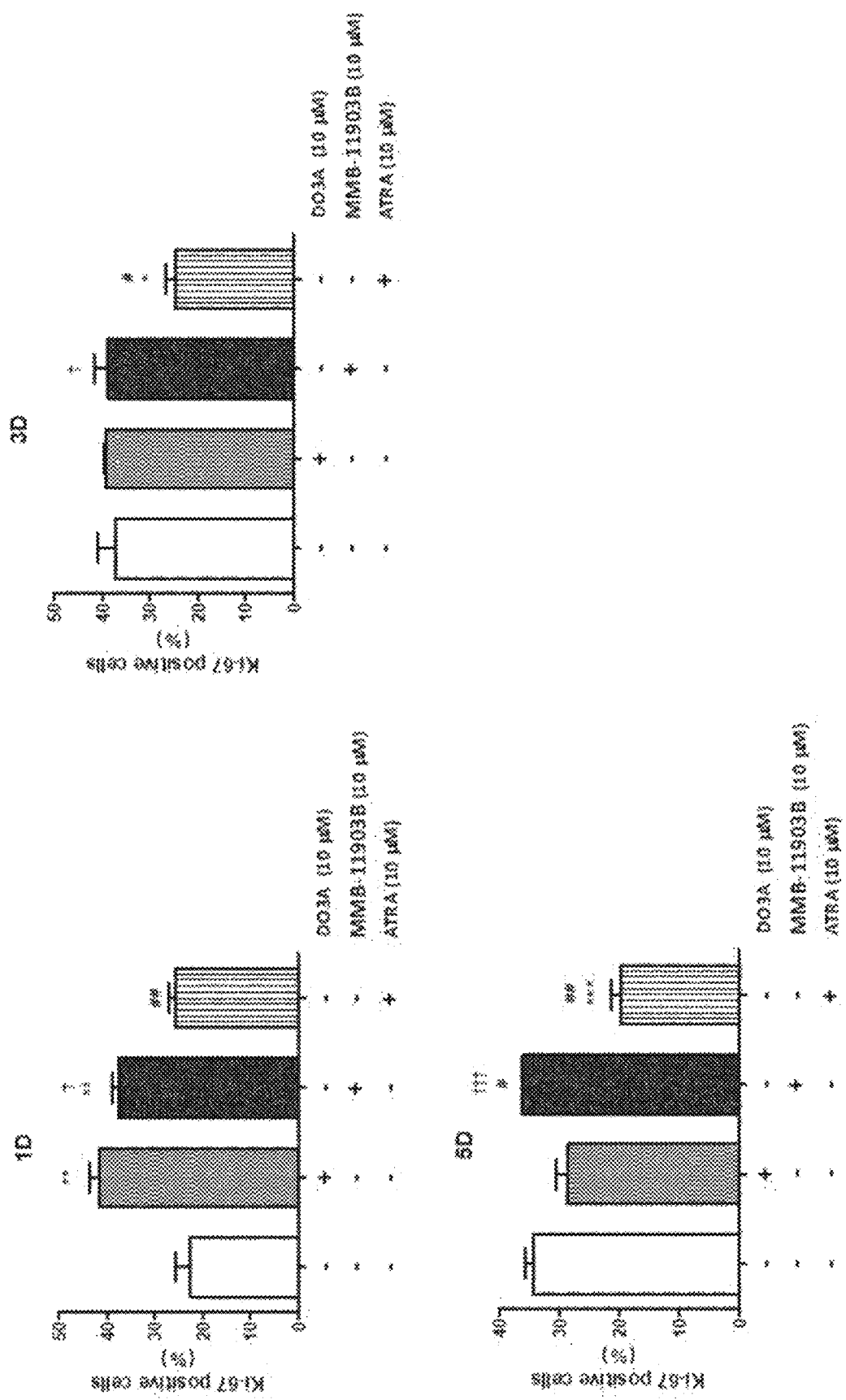

FIG. 7A is an image obtained using fluorescence microscopy after a nerve cell line treated with each of DO3A, ATRA, and MMB-11903B according to the present disclosure is stained with a marker for cell proliferation. FIG. 7B is a graph showing a percentage of the number of positive cells using Ki-67 antibody to examine proliferation of nerve cells treated with each of DO3A, ATRA, and MMB-11903B according to the present disclosure.

DETAILED DESCRIPTION OF THE INVENTION

The terminology used herein is for the purpose of describing particular embodiments only and is not intended to be limiting of the present disclosure. Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

According to one aspect of the present disclosure, a compound represented by a following Chemical Formula 1 is provided

[Chemical Formula 1]

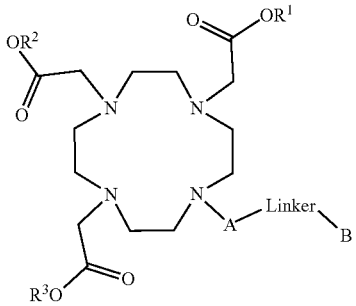

In the Chemical Formula 1, each of $R_1$ to $R_3$ independently represents hydrogen, linear or branched (C1-C10) alkyl, or an electron pair to form any bond. Specifically, in the Chemical Formula 1, each of $R_1$ to $R_3$ may independently represent hydrogen, linear or branched (C1-C3)alkyl, or an electron pair for forming any bond. More specifically, in the Chemical Formula 1, each of $R_1$ to $R_3$ may independently represent hydrogen or a pair of electrons to form an any bond. Even more specifically, in the Chemical Formula 1, each of $R_1$ to $R_3$ may independently represent hydrogen.

Further, in the Chemical Formula 1, A represents *—$(CH_2)_n$-$A^1$-*.

Further, in the Chemical Formula 1, n represents an arbitrary integer from 0 to 5. Specifically, in the Chemical Formula 1, n may represent an arbitrary integer from 1 to 5. More specifically, n may be an arbitrary integer from 1 to 3.

Further, in the Chemical Formula 1, A1 represents *—COO—*, *—CO—*, *—$NR^4$—*, *—$CH_2$—*, *—CONH—*, or *—O—*. Specifically, A1 may represent *—COO—*, *—CO—*, *—$NR^4$—*, or *—CONH—*, and more specifically, *—CONH—*.

Further, in the Chemical Formula 1, Linker represents *-$L^1$-NHCO-$L^2$-*, *-$L^1$-O—R—O-$L^2$-*, *-$L^1$-$CH_2$-$L^2$-*, *-$L^1$-$NR^5$-$L^2$-*, or *-$L^1$-COO-$L^2$-*. Specifically, Linker may represent *-$L^1$-NHCO-$L^2$-*, or *-$L^1$-$NR^5$-$L^2$-*. More specifically, Linker may represent *-$L^1$-NHCO-$L^2$-*.

Further, in the Chemical Formula 1, $L^1$ represents linear or branched (C1-C30)alkyl. Specifically, $L^1$ may represent linear or branched (C1-C10)alkyl, more specifically, linear or branched (C1-C5)alkyl.

Further, in the Chemical Formula 1, $L^2$ represents a single bond or linear or branched (C1-C30)alkyl. Specifically, $L^2$ may represent a single bond, or linear or branched (C1-C10) alkyl. More specifically, $L^2$ may represent a single bond, or linear or branched (C1-C5)alkyl. Even more specifically, $L^2$ may represent a single bond.

Further, in the Chemical Formula 1, R represents linear or branched (C1-C20)alkyl. Specifically, R may represent linear or branched (C1-C10)alkyl, more specifically, linear or branched (C1-C5)alkyl.

Further, in the Chemical Formula 1, each of $R^4$ and $R^5$ independently represent hydrogen or linear or branched (C1-C10)alkyl. Specifically, each of $R^4$ and $R^5$ may independently represent hydrogen or linear or branched (C1-C5) alkyl. More specifically, $R^4$ may be hydrogen. Further, more specifically, $R^5$ may be hydrogen.

Further, in the Chemical Formula 1, B represents a moiety derived from retinoic acid. The retinoic acid may include isomers of retinoic acid such as all-trans retinoic acid (hereinafter, referred to as ATRA), 13-cis retinoic acid, 9-cis retinoic acid, and the like. Specifically, B may represent a compound represented by a following Chemical Formula 2a, 2b, or 2c:

[Chemical Formula 2a]

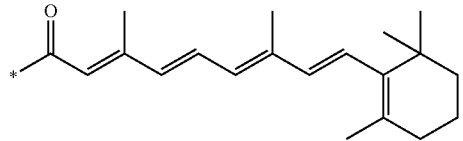

-continued

[Chemical Formula 2b]

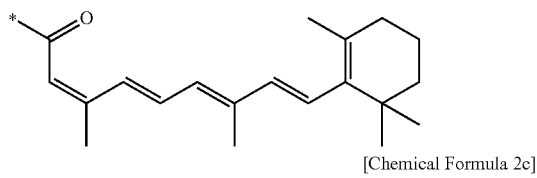

[Chemical Formula 2c]

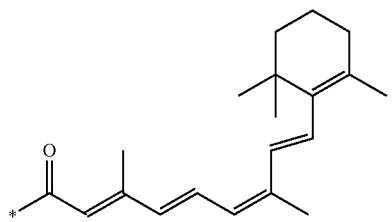

The compound represented by the Chemical Formula 2a is a moiety derived from ATRA. The compound represented by the Chemical Formula 2b is a moiety derived from 13-cis retinoic acid. The compound represented by the Chemical Formula 2c is a moiety derived from 9-cis retinoic acid.

According to one implementation of the present disclosure, B in the Chemical Formula 1 may represent the compound represented by the Chemical Formula 2a.

According to another implementation of the present disclosure, in the Chemical Formula 1 of the compound according to the present disclosure, n may represent an arbitrary integer from 1 to 5, and $A^1$ may represent *—CONH—*.

According to another implementation of the present disclosure, in the Chemical Formula 1 of the compound according to the present disclosure, the Linker may represent *-$L^1$-$NR^5$-$L^2$-*, and $R^5$ may be hydrogen.

According to another implementation of the present disclosure, in the Chemical Formula 1 of the compound according to the present disclosure, $L^1$ may represent linear or branched (C1-C10)alkyl, and $L^2$ may represent a single bond.

According to another implementation of the present disclosure, in the Chemical Formula 1 of the compound according to the present disclosure, each of $R^1$ to $R^3$ may independently represent hydrogen, linear or branched (C1-C3) alkyl, or an electron pair to form any bond, A may represent *—$(CH_2)_n$-$A^1$-*, n may represent any integer from 1 to 5, $A^1$ may represent *-C00-*, *—CO—*, *—$NR^4$—*, or *—CONH—*, Linker may represent *-$L^1$-NHCO-$L^2$-* or *-$L^1$-$NR^5$-$L^2$-*, $L^1$ may represent linear or branched (C1-C10)alkyl, $L^2$ may represent a single bond or linear or branched (C1-C10)alkyl, R may represent linear or branched (C1-C10)alkyl, each of $R^4$ and $R^5$ may independently represent hydrogen or linear or branched (C1-C5)alkyl, and B may be represented by the Chemical Formula 2a, 2b, or 2c.

According to another implementation of the present disclosure, in the Chemical Formula 1 of the compound according to the present disclosure, each of $R^1$ to $R^3$ may independently represent hydrogen, or an electron pair to form any bond, A may represent *—$(CH_2)_n$-$A^1$-*, n may represent any integer from 1 to 3, $A^1$ may represent *—CONH—*, Linker may represent *-$L^1$-$NR^5$-$L^2$-*, $L^1$ may represent linear or branched (C1-C10)alkyl, $L^2$ may represent a single bond, R may represent linear or branched (C1-C10)alkyl, each of $R^4$ and $R^5$ may independently represent hydrogen, and B may be represented by the Chemical Formula 2a, 2b, or 2c.

The compound of the Chemical Formula 1 according to the present disclosure may be prepared by, for example, reacting a compound of a following Chemical Formula 1-1 with a retinoic acid derivative. In this regard, the retinoic acid derivative may be a precursor of $L^2$ defined in the Chemical Formula 1. For example, the retinoic acid derivative may have a structure in which succinimide is bound to retinoic acid.

[Chemical Formula 1-1]

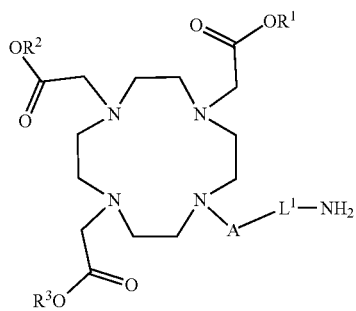

In the Chemical Formula 1-1, each of A and $L^1$ is the same as defined in the Chemical Formula 1.

According to one aspect of the present disclosure, there is provided a pharmaceutical composition containing the compound of the Chemical Formula 1 as aforementioned, or a pharmaceutically acceptable salt thereof.

The compound of the Chemical Formula 1 according to the present disclosure is useful to induce or promote the generation of neurites, growth of neurites, differentiation of nerve cells, regeneration of nerve cells, and/or proliferation of nerve cells against neuronal damage, neurological disease, or developmental disorder.

The term "neurite" refers to a projection from a cell body of a nerve cell, including, for example, axons and dendrites.

Accordingly, according to one aspect of the present disclosure, a pharmaceutical composition containing the compound according to the present disclosure or a pharmaceutically acceptable salt thereof is provided which is capable of inducing or promoting generation of neurites, growth of neurites, differentiation of neurons, regeneration of neurons, and/or proliferation of nerve cells.

Further, according to another aspect of the present disclosure, there is provided a method of inducing or promoting generation of neurites, growth of neurites, differentiation of neurons, regeneration of neurons, or proliferation of neurons, the method including administering the compound according to the present disclosure or a pharmaceutically acceptable salt thereof to a subject in need of neurite generation, neurite growth, nerve cell differentiation, nerve cell regeneration, or neuronal proliferation or to nerve cells.

Further, according to one aspect of the present disclosure, a pharmaceutical composition for treating or preventing neuronal damage, neurological disease, or developmental disorder is provided, wherein the composition is characterized in that it contains the compound according to the present disclosure or a pharmaceutically acceptable salt thereof.

As used herein, the term "treatment" may mean achievement of a desired therapeutic effect on a subject, and may include reducing progression of a disease, stopping the progression thereof, alleviating symptoms thereof, ameliorating a condition thereof, and curing the condition thereof.

The compound according to the present disclosure may provide a fundamental cure of a disease via morphological and functional restoration of damaged cells, and thus the treatment specifically refers to the treatment of the disease via morphological and functional restoration of the nerve cells. Further, the term "prevention" may refer to use in a subject in which the disease is not yet developed but may be potentially developed.

The term "neuronal damage" refers to any damage to the nervous system, such as spinal cord injury or optic neuronal damage. This includes, for example, damage to the nervous system caused by trauma, chemically (e.g., by a neurotoxin or by a treatment regimen having an immunosuppressive effect), or caused by a disease or disorder. Further, the neuronal damage includes damage to the central nervous system (CNS) and damage to the peripheral nervous system (PNS), more specifically, cranial neuronal damage, spinal cord damage, optic neuronal damage, and peripheral neuronal damage.

The term "neurological disease" includes degenerative neurological diseases, ischemic neurological diseases, and peripheral neurological diseases. The "degenerative neurological disease" specifically includes degenerative brain diseases (e.g., memory loss, dementia, Alzheimer's disease, Parkinson's disease, Huntington's disease, etc.), amyotrophic lateral sclerosis (ALS), ataxia, epilepsy, and the like. The "ischemic neurological disease" specifically includes ischemic brain disease (e.g., ischemic stroke). The "peripheral neurological disease" specifically includes polyneuropathy, mononeuropathy, polymononeuritis, and autonomic neuropathy.

The term "developmental disorder" includes brain neurodevelopmental disorders.

As may be identified in Example to be described later, the compound according to the present disclosure may generate and grow neurites of nerve cells and differentiate, regenerate, and proliferate the nerve cells. Thus, the pharmaceutical composition containing the compound or a pharmaceutically acceptable salt thereof may be used for treating or preventing neuronal damage, neurological disease, or developmental disorder. In addition, the compound according to the present disclosure may be very usefully used as a learning ability enhancer or cognitive function improver.

Further, according to another aspect of the present disclosure, a method for treating or preventing neuronal damage, neurological disease, or developmental disorder is provided, the method including administering the compound according to the present disclosure or a pharmaceutically acceptable salt thereof to a subject in need of treatment or prevention of neuronal damage, neurological disease, or developmental disorder.

According to one implementation of the present disclosure, a pharmaceutical composition for treating or preventing brain neuronal damage, degenerative brain disease, or ischemic brain disease is provided, the composition containing the compound according to the present disclosure or a pharmaceutically acceptable salt thereof.

According to another implementation of the present disclosure, a pharmaceutical composition for treatment or prevention of dementia, Alzheimer's disease, Parkinson's disease, Huntington's disease, epilepsy, memory loss, or ischemic stroke is provided, the composition containing the compound according to the present disclosure or a pharmaceutically acceptable salt thereof.

According to another implementation of the present disclosure, a pharmaceutical composition for treating or preventing peripheral neuronal damage, spinal cord damage, optic neuronal damage, amyotrophic axonal sclerosis, ataxia, a peripheral nerve disease is provided, the composition containing the compound according to the present disclosure or a pharmaceutically acceptable salt thereof.

According to another implementation of the present disclosure, there is provided a pharmaceutical composition for treating or preventing brain neurodevelopmental disorders, the composition being characterized in that it contains the compound according to the present disclosure or a pharmaceutically acceptable salt thereof.

In the pharmaceutical composition of the present disclosure, the compound of the Chemical Formula 1 according to the present disclosure may be used in a form of a pharmaceutically acceptable salt. The "pharmaceutically acceptable salt" refers to a compound salt that retains pharmacological activity of a parent compound. For example, the pharmaceutically acceptable salt may include (i) salts formed with inorganic acids such as hydrochloric acid, hydrobromic acid, sulfuric acid, nitric acid, and phosphoric acid; (ii) salts formed with organic acids such as acetic acid, propionic acid, isobutyric acid, glycolic acid, lactic acid, pyruvic acid, malonic acid, succinic acid, glutaric acid, fumaric acid, malic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid; (iii) salts formed when acidic protons present in the parent compound are replaced with metal ions, such as alkali metal ions, alkaline earth metal ions, or aluminum ions; (iv) coordinates with organic bases such as ethanolamine, diethanolamine, triethanolamine, N-methylglucamine; or (v) a salt of an amino acid such as alginate.

Further, the pharmaceutical composition according to the present disclosure may contain an isomer, solvate, or prodrug of the compound of the Chemical Formula 1 of the present disclosure. As used herein, the term "isomer" includes all possible stereochemical isomers, including diastereomers and enantiomers. The compound in accordance with the present disclosure should be understood to refer to a mixture of all possible stereochemically isomeric forms. Further, the term "solvate" refers to a complex of a solute (e.g., the compound of the Chemical Formula 1) and a solvent. When the solvent is water, the solvate may be referred to as a hydrate. As used herein, the term "prodrug" refers to a compound that is converted into an active compound having a medicinal effect via bio-absorption and metabolism after being administered into the body. The prodrug may be a compound that is either inactive by itself or is less active than an active compound, and may be favorable in terms of handling, administration, or metabolism. The prodrug may be in a form of an ester (e.g., a physiologically acceptable and metabolically labile ester) of the active compound, a sugar derivative thereof, or an amino acid ester derivative thereof.

The pharmaceutical composition according to the present disclosure may include the compound represented by the Chemical Formula 1 or a pharmaceutically acceptable salt thereof alone, or may further include a pharmaceutically acceptable carrier in addition thereto. The pharmaceutically acceptable carrier may be one commonly used in the pharmaceutical field, and may include an excipient (e.g., starch, calcium carbonate, sucrose, lactose, sorbitol, mannitol, cellulose, etc.) or a diluent (e.g., physiological saline, purified water, etc.).

Further, if necessary, the pharmaceutical composition according to the present disclosure may further contain pharmaceutically acceptable excipients other than the pharmaceutically acceptable carrier, for example, binder, disintegrant, lubricant, coating agent, film coating base, enteric film coating base, soft capsule base, solubilizer, emulsifier, suspending agent, stabilizer, buffer, antioxidant, surfactant, sweetener, flavoring agent, preservative, thickener, flavoring agent, or coloring agent.

The pharmaceutical composition according to the present disclosure may be administered orally or parenterally. The parenteral administration may include intravenous injection, subcutaneous injection, intramuscular injection, intraperitoneal injection, endothelial administration, topical administration, intranasal administration, intrapulmonary administration, and rectal administration. For the oral administration, the pharmaceutical composition according to the present disclosure may be formulated in a form of a solid or liquid formulation. The solid formulation may include, for example, tablets, capsules (soft & hard capsules), powders, granules, pills, troches, and the like. The liquid formation may include, for example, elixirs, suspensions, emulsions, solutions, syrups, or lemonades. The tablet may further contain, in addition to the active ingredient, carriers such as lactose and corn starch, lubricants such as magnesium stearate, binders such as methylcellulose, microcrystalline cellulose, polyvinyl alcohol, etc., and disintegrants such as bentonite and sodium alginate. For the liquid formulation, the active ingredient may be formulated together with a carrier such as purified water or physiological saline, and if necessary, a solubilizing agent such as monostearate sucrose, and a stabilizer such as polyvinylpyrrolidone. For an aqueous suspension for oral use, the active ingredient may be formulated together with a suspending agent and, if necessary, a surfactant, preservative, stabilizer, and the like.

A dosage of the pharmaceutical composition according to the present disclosure may be determined in consideration of the administration method, an age, a sex, disease severity, a condition of a patient, an inactivation level, and drugs used in combination therewith, and may be administered once or divided into several doses.

Hereinafter, for a detailed understanding of the present disclosure, a compound according to the present disclosure, a preparation method thereof, and characteristics of a pharmaceutical composition containing the same will be described based on a representative compound according to the present disclosure. However, the present disclosure is not limited to following Examples.

1. Preparation Example of Compound According to the Present Disclosure

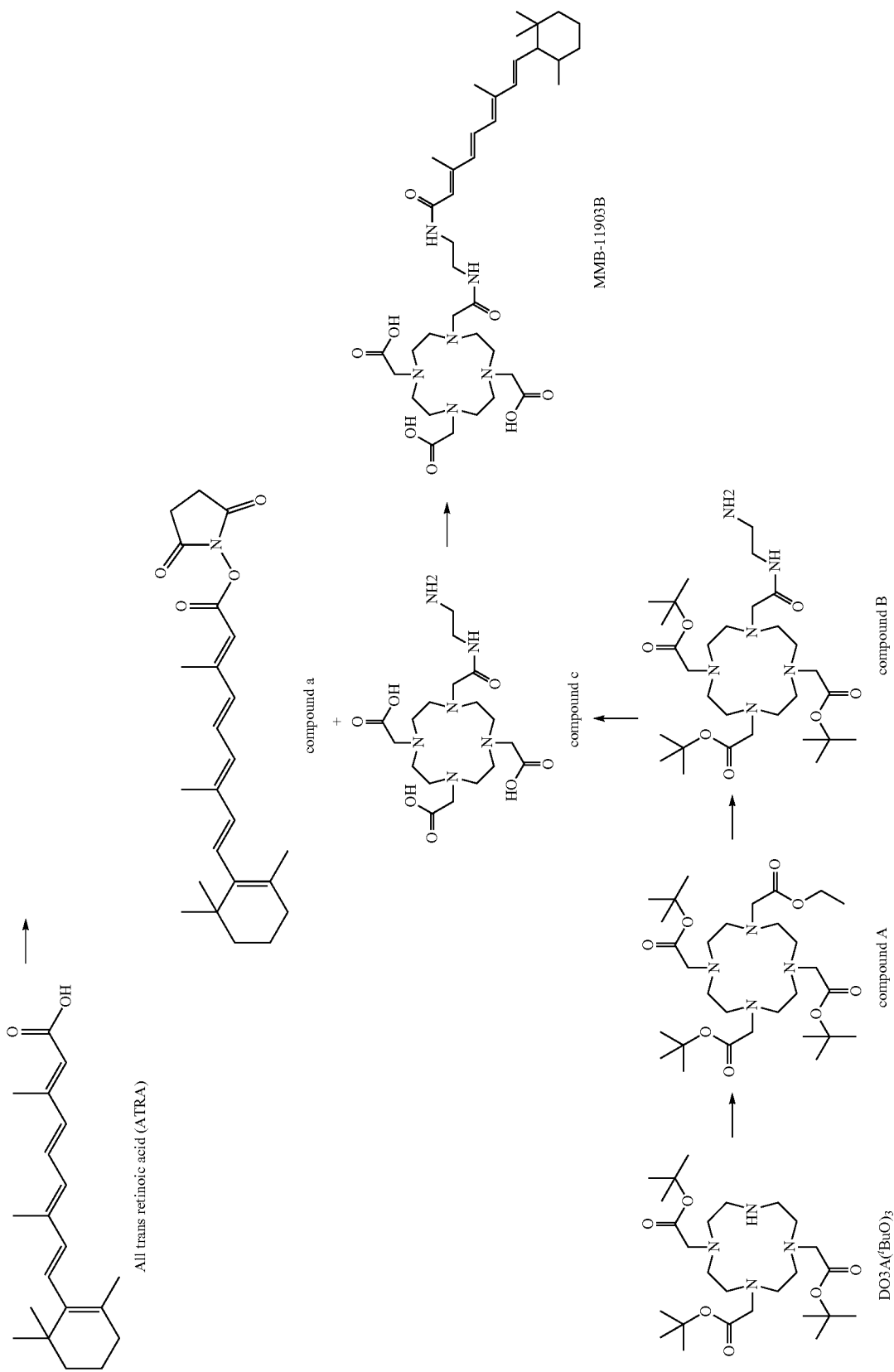

1) Synthesis of Compound a

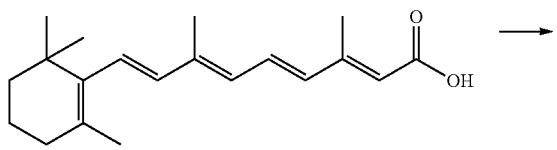
All trans retinoic acid (ATRA)

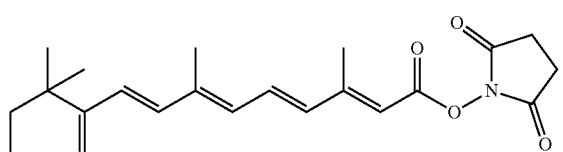
Compound a

All trans retinoic acid (4 g, 13.31 mmol) was dissolved in 90 ml of TH to produce a mixed solution, DCC (4.12 g, 19.97 mmol) was added thereto, and then the mixed solution was stirred for 30 minutes. A solution in which N-hydroxysuccinimide (NHS) (2.30 g, 19.97 mmol) was dissolved in 30 ml of THF was added dropwise thereto at 4° C., followed by reaction at room temperature for 18 hours. A resulting solid was filtered, the solvent was removed therefrom, and a filtrate was dissolved again in dichloromethane (DCM) to produce a solution which in turn passed through a silica gel column to purify compound a. Yield: 4.6 g (87.0%)

2) Synthesis of Compound A

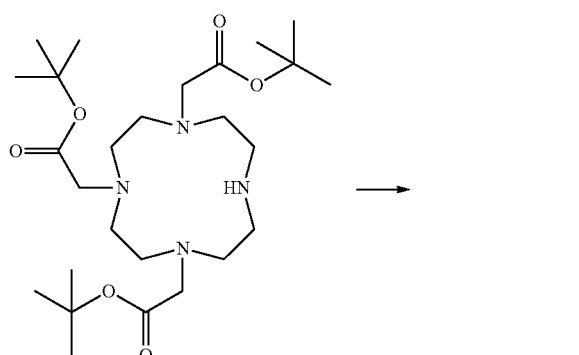
DO3A(ᵗBuO)₃

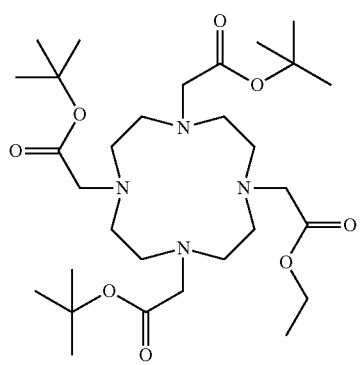
Compound A

DO3A(ᵗBuO)₃ (10 g, 19.43 mmol) was dissolved in 320 ml of acetonitrile (ACN) to produce a mixed solution, and KHCO₃ (5.93 g, 59.26 mmol) was added thereto, followed by stirring at room temperature for 30 minutes. Ethyl bromoacetate (2.36 ml, 21.37 mmol) was added dropwise thereto, and then the mixed solution was stirred at 70° C. for 24 hours, and an inorganic salt was filtered, and the solvent was removed from a reaction product which in turn was vacuum dried to obtain compound A as a yellow solid. Yield: 11.5 g (99%)

3) Synthesis of Compound B

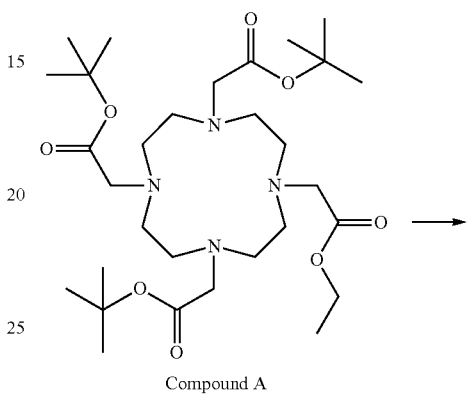
Compound A

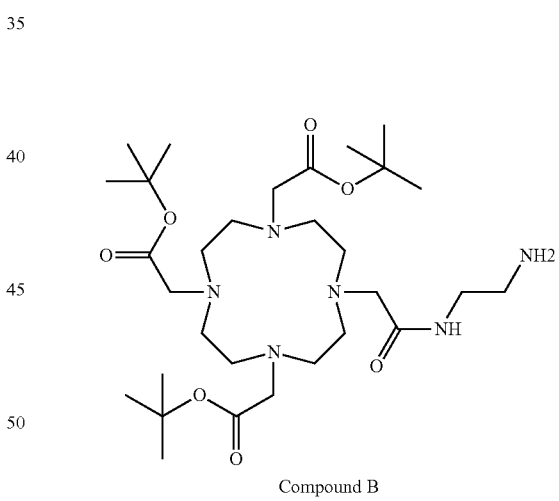
Compound B

Ethylenediamine (60 ml, 846.1 mmol) was added to the compound A (25.4 g. 42.30 mmol) to produce a mixture, followed by stirring thereof at room temperature for 4 days. After completion of a reaction, 150 ml of brine solution was added thereto, and the mixture was subjected to extraction three times with 150 ml of DCM solution to obtain an organic solvent layer. Dehydration was performed using Na₂SO₄, and the solvent was removed therefrom, and a resultant was purified using column chromatography under a DCM/MeOH eluent condition. Hexane was added to a thus-obtained compound which in in turn was stirred at room temperature to obtain compound B as a white solid. Yield: 10.43 g (40.2%).

4) Synthesis of Compound C

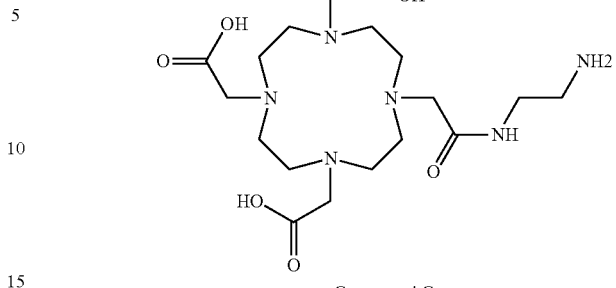

Compound C

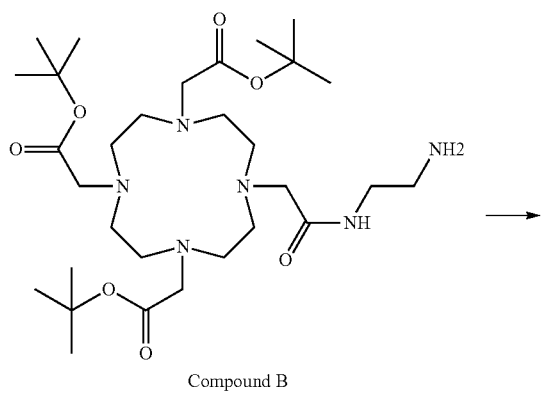

Compound B

The compound B (3 g, 4.88 mmol) was dissolved in DCM (12 ml/48 ml, v/v) containing 20% trifluoroacetic acid (TFA) to produce a mixed solution which in turn was heated under reflux at 40° C. for reaction for 24 hours. The solvent was repeatedly evaporated therefrom under reduced pressure while adding MeOH thereto, and then a resulting product was dissolved again in MeOH and then a mixed solution was subjected to precipitation in ethyl ether. A thus-obtained white solid was dissolved in distilled water and a mixed solution was subjected to re-precipitation in acetone to obtain purified compound C as a white solid. Yield: 1.37 g (62.9%)

5) Synthesis of Compound MMB-11903B

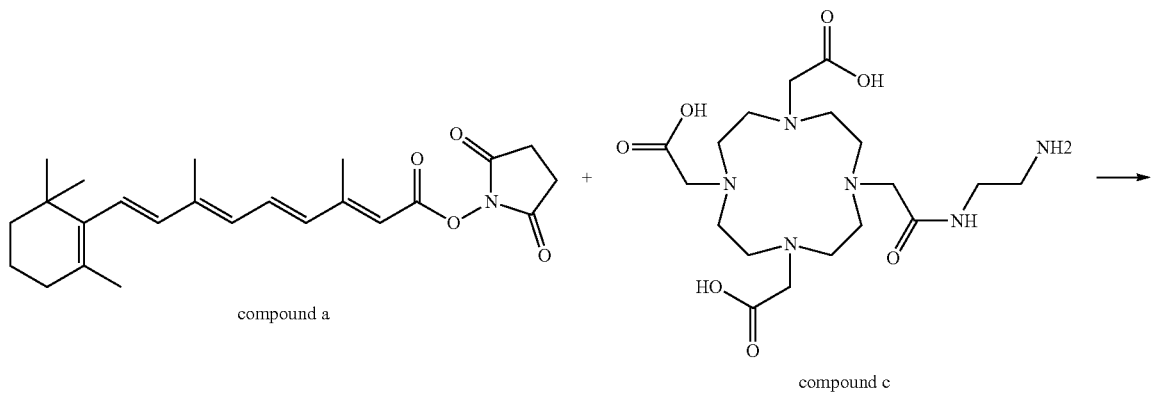

compound a + compound c

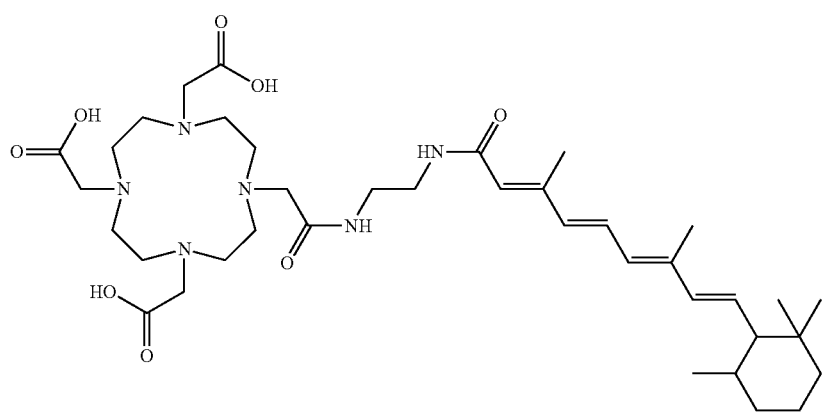

MMB-11903B

The Compound C (0.2 g, 0.36 mmol) was dissolved in MeOH to produce a mixed solution and then N,N-diisopropylethylamine (DIPEA) (0.62 ml, 3.57 mmol) was added thereto, followed by stirring thereof at room temperature for 3 hours. The compound a (0.17 g, 0.43 mmol) was added thereto, and the mixed solution was heated under reflux at 60° C. for 24 hours, and then was subjected to precipitation in ethyl ether to obtain a compound as a pale yellow solid. Isopropyl alcohol (IPA) was added to the above compound to produce a mixed solution which in turn was heated, and then was cooled to produce a resulting compound which in turn was filtered to obtain Compound MMB-11903B. Yield: 0.09 g (34.3%)

2. Solubility Test

In order to check the solubility of the compound according to the present disclosure, each of MMB-11903B according to the present disclosure prepared in the Preparation Example and ATRA was added to 1 mL of deionized water at a concentration of 100 mM (Compound MMB-11903B according to the present disclosure: 72.8 mg/mL; ATRA: 30.0 mg/mL) and each mixed solution was stirred for dissolution by lightly vortexing the same. A state immediately after the dissolution is photographed and shown in FIG. 1. After each of the prepared solution of the compound MMB-11903B according to the present disclosure and the prepared ATRA solution was left at room temperature for 20 minutes, an image thereof was taken again to observe a dissolution state of each compound in each solution (FIG. 1).

Figure 1:
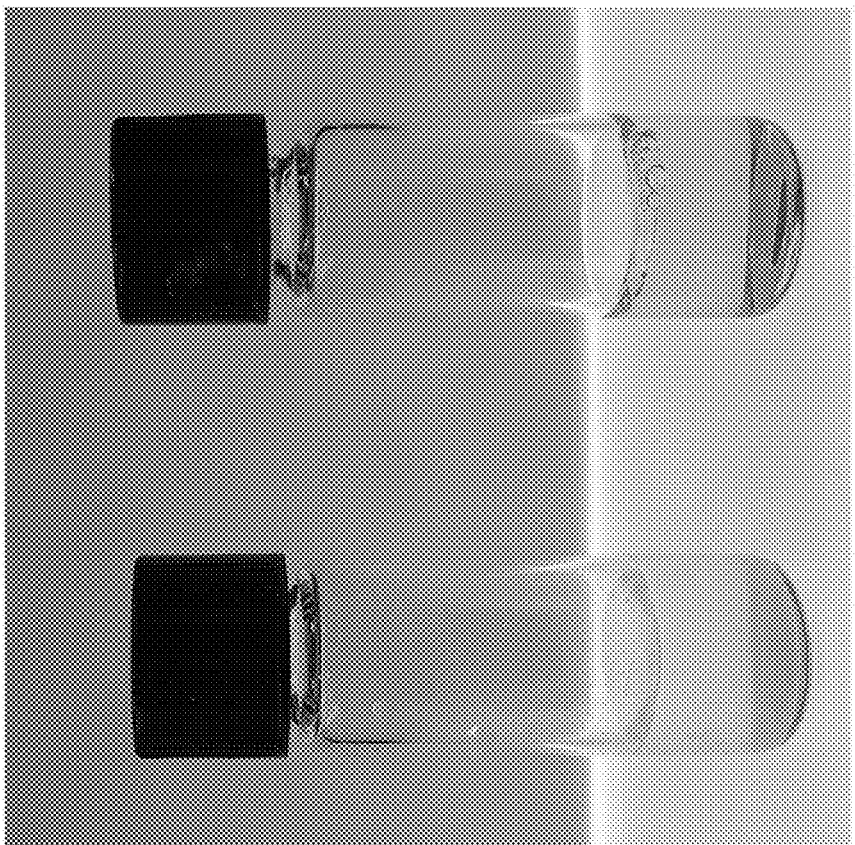
FIG. 1 is a photograph showing a state immediately after each of a compound according to the present disclosure (MMB-11903B) and ATRA (comparative compound, all-trans retinoic acid) is dissolved in water, and a dissolution state after each of the two compounds is allowed to be left for 20 minutes.

As may be identified in FIG. 1, each of the compound MMB-11903B in accordance with the present disclosure and ATRA was uniformly dissolved in the solution initially. However, ATRA was separated from the solvent and was precipitated over time, whereas although the solution of the compound MMB-11903B was allowed to be left for the same time as the solution of ATRA was, the compound MMB-11903B was not separated from the solvent and was able to maintain a uniform dissolution state. Thus, the compound MMB-11903B according to the present disclosure may be easily dissolved in the solvent such as water, so that it has high solubility, and further has solubility stability, so that it may maintain a dissolved state even after being left for a long time. Thus, it may be identified that the solubility and dissolution stability of the compound MMB-11903B according to the present disclosure are very excellent when compared to those of ATRA.

3. Cytotoxicity Test 3-1) Cell Viability Test

Cell viability analysis of a nerve cell line using CCK-8 was performed on human neuroblastoma SH-SY5Y as an undifferentiated nerve cell line. For reference, the analysis using the CCK-8 (Cell counting kit-8) was based on a highly water-soluble tetrazolium salt-SST-8. The analysis is based on the fact that when [2-(2-methoxy-4-nitrophenyl)-3-(4-nitrophenyl)(2,4-disulfophenyl)-2H-tetrazolium, monosodium salt] is reduced under presence of an electron mediator, a water-soluble formazan orange dye is produced, and an amount of the formazan dye produced by dehydrogenase in cells is directly proportional to the number of living cells. The specific experimental method is as follows.

SH-SY5Y was grown in Minimum Essential Medium (MEM) medium supplemented with 10% Fetal bovine serum (FBS), 1% Antibiotic-Antimycotic (AA), and 2 mM L-Glutamine. For cell viability analysis, stabilized cells were suspended in 200 µL of the medium at a density of $1 \times 10^4$ cells/well and planted in each well of a 96-well plate. The cells were attached to a 37° C., 5% $CO_2$ incubator and was allowed to be left so as to be stabilized for at least 14 hours. The next day, the growth medium was removed therefrom. 100 µL of Dulbecco's Modified Eagle Medium/Nutrient Mixture F-12 (DMEM/F-12=1:1) medium supplemented with 1% FBS, 1% AA, and 2 mM L-Glutamine for differentiation induction was diluted with each of the compound MMB-11903B acceding to the present disclosure synthesized in the Preparation example and all-trans-Retinoic acid (hereinafter, ATRA) as a compound for comparison to various concentrations (0, 1, 2, 5, 10, 20, 30, and 50 µM). Then, the cells were incubated therein for 24, 48, 72 hours, and under at 37° C. and 5% $CO_2$ condition. At 2 hours before a harvest time, 10 µL of CCK-8 solution was added to each well and the cells were incubated for an additional 2 hours. Absorbance of the plate in which the cell culture was completed was measured at 450 nm using a microplate reader.

Cell viability (%)=$B/A$×100(%) [Cell viability calculation equation]

(In the equation, A denotes an absorbance value measured in a control well, and B denotes an absorbance value measured in the well containing the drug).

The calculated values were graphed using the GraphPad Prism application. The statistical significance of the obtained values was identified via one-way ANOVA with Dunnett's multiple comparison test. *$p<0.5$, ***$p<0.01$ vs. 24 h control, #$p<0.5$, ###$p<0.01$ vs. 48 h control, †††$p<0.01$ vs. 72 h control indicates significance. The results about ATRA and the compound MMB-11903B according to the present disclosure are shown in FIG. 2A and FIG. 2B, respectively.

Figure 2A:
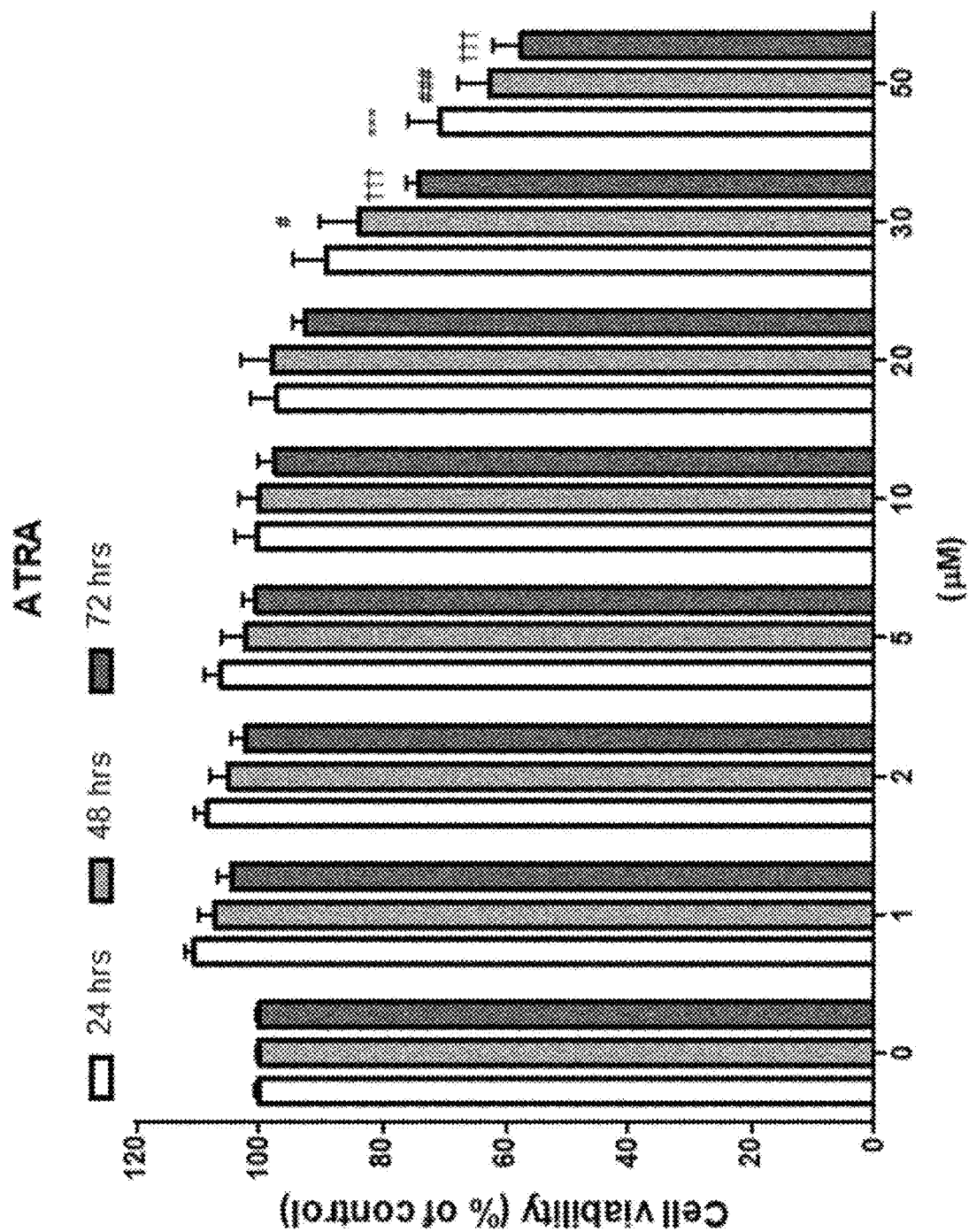
FIG. 2A is a graph showing a nerve cell viability based on a concentration of ATRA and an elapsed time.
Figure 2B:
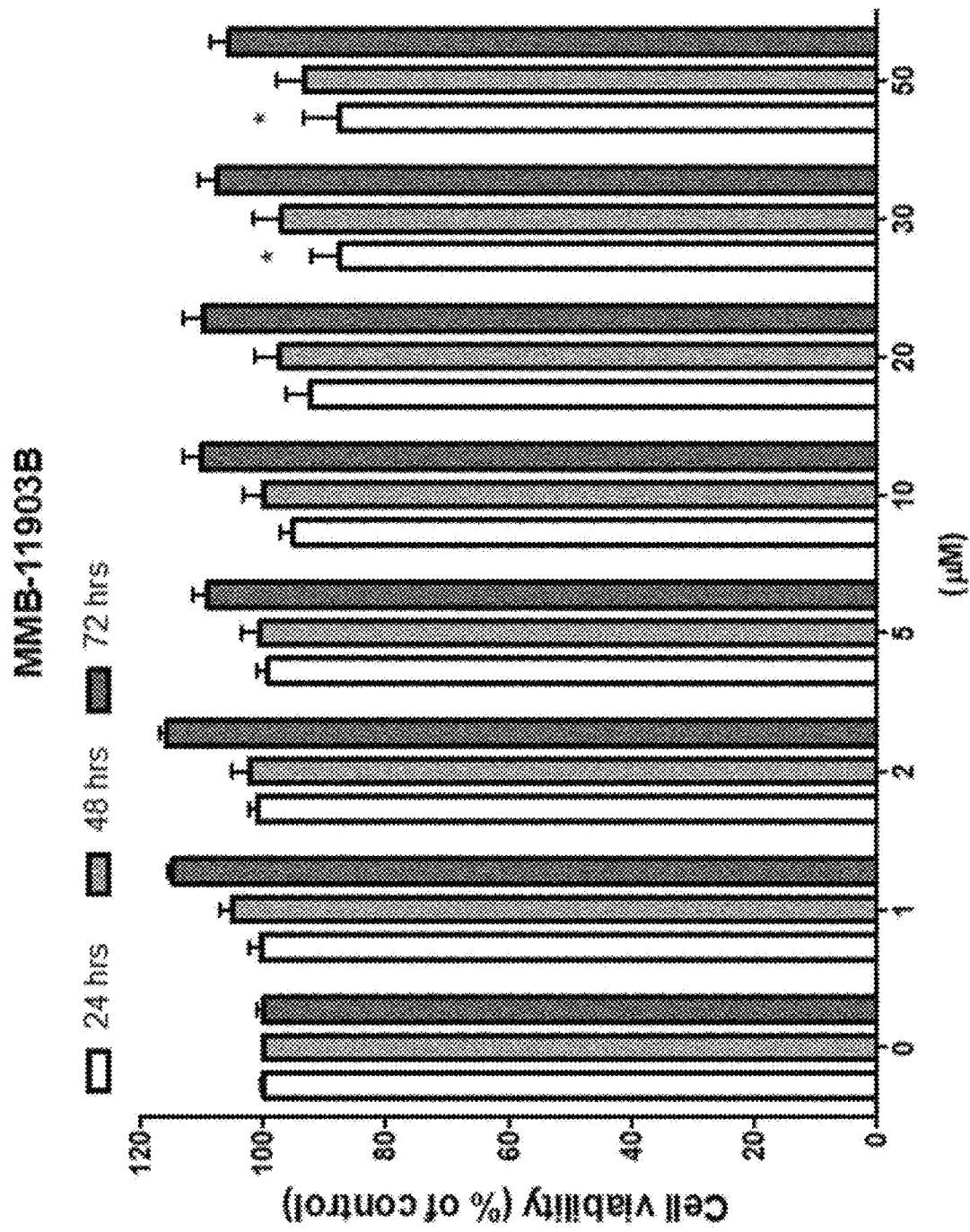
FIG. 2B is a graph showing a nerve cell viability based on a concentration of a MMB-11903B compound and an elapsed time.

In FIG. 2A and FIG. 2B, each of 24 hour viability, 48 hour viability, and 72 hour viability when the concentration of each of ATRA and compound MMB-11903B was 0 M (that is, when no ATRA or compound MMB-11903B was administered) was set as 100%. In this regard, the higher the concentration of ATRA and the longer the time, the lower the cell viability (see FIG. 2A). On the contrary, it may be identified that the 72-hour viability when the compound MMB-11903B according to the present disclosure is administered is always higher than that when it is not administered. Thus, it may be identified that the compound MMB-11903B according to the present disclosure may further increase the cell viability as the administration time elapses. In particular, the 72-hour viability at a concentration of 50 µM of the compound MMB-11903B according to the present disclosure was approximately two times higher than the 72-hour viability at a concentration of 50 µM of ATRA. Thus, it was identified that despite the long-term exposure of MMB-11903B to the nerve cells, the toxicity to the nerve cells was reduced.

3-2) Cytotoxicity Test Using Lactate Dehydrogenase (LDH) Analysis

Cytotoxicity (cell death) may be measured indirectly via a cell viability test. However, for more sensitive and accurate measurement, the cytotoxicity may be verified based on a method using an enzyme related to apoptosis or cell damage. Lactate dehydrogenase (LDH) is a stable enzyme present in the cytoplasm, and is not normally discharged out of the cell because it cannot pass through the cell membrane, but is released into the medium when the cell membrane is damaged or the cell dies. Therefore, an amount of LDH in the medium is proportional to the number of dead or injured cells and thus is measured.

SH-SY5Y was grown in Minimum Essential Medium (MEM) medium supplemented with 10% Fetal bovine serum (FBS), 1% Antibiotic-Antimycotic (AA), and 2 mM L-Glutamine. For cell viability analysis, stabilized cells were suspended in 200 μL of the medium at a density of 2.5×10⁴ cells/well and planted in each well of a 96-well plate. The cells were attached to a 37° C., 5% $CO_2$ incubator and was allowed to be left so as to be stabilized for at least 14 hours. The next day, the growth medium was removed therefrom. 100 μL of Dulbecco's Modified Eagle Medium/Nutrient Mixture F-12 (DMEM/F-12=1:1) medium supplemented with 1% FBS, 1% AA, and 2 mM L-Glutamine for differentiation induction was diluted with each of the compound MMB-11903B acceding to the present disclosure synthesized in the Preparation example and all-trans-Retinoic acid (hereinafter, ATRA) as a compound for comparison to various concentrations (0, 1, 5, 10, 20, 30, 50, 100, and 200 μM). Then, the cells were incubated therein for 24, 48, 72 hours, and under at 37° C. and 5% C02 condition. 10 μL of a top layer of the culture medium was dispensed into a new 96-well plate, and 100 μL of a LDH reaction mixture (D-Plus™ LDH kit, Cat. No. LDH-500) was added thereto, followed by reaction in a dark state for 30 minutes. Absorbance of the plate in which the reaction was completed was measured at 450 nm using a microplate reader.

Cytotoxicity (%)=
(A−B)/(C−B)×100(%)   [Cytotoxicity calculation equation]

(In the above equation, A denotes an absorbance value of a drug-injected group, B denotes an absorbance value of a drug-free group, and C denotes an absorbance value measured at a maximum amount of LDH that can be released from the cells by adding 10 μL of lysis solution to the cells used in the experiment)

The calculated values were graphed using the GraphPad Prism application. The statistical significance of the obtained values was identified via one-way ANOVA with Dunnett's multiple comparison test. ***$p<0.01$ vs. 24 h control, ###$p<0.01$ vs. 48 h control, †$p<0.5$, †††$p<0.01$ vs. 72 h control indicate presence of statistical significance. The results about ATRA and the compound MMB-11903B according to the present disclosure are shown in FIG. 3A and FIG. 3B, respectively.

Figure 3A:
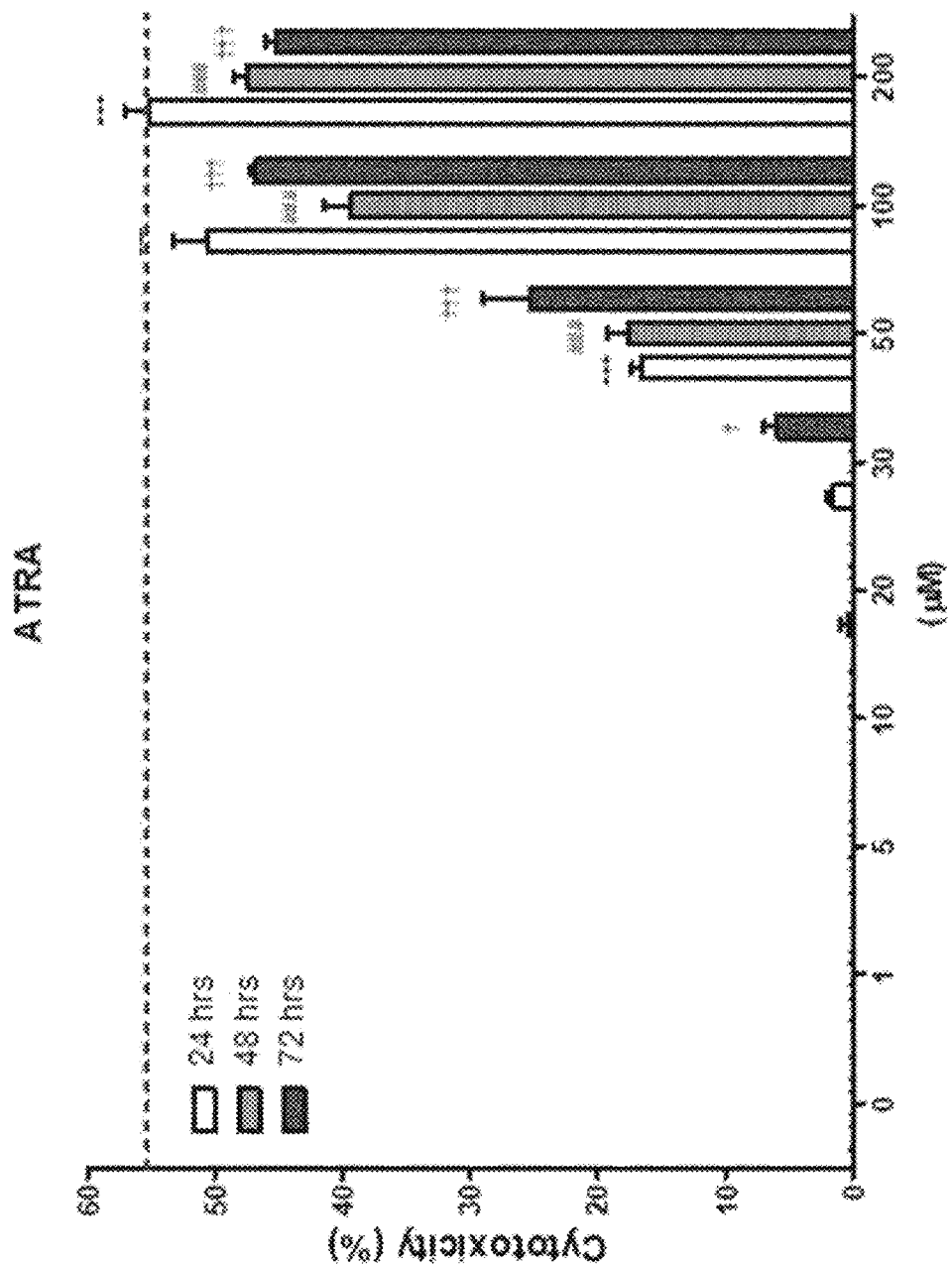
FIG. 3A is a graph showing neuronal cytotoxicity based on a concentration of ATRA and an elapsed time, and FIG.
Figure 3B:
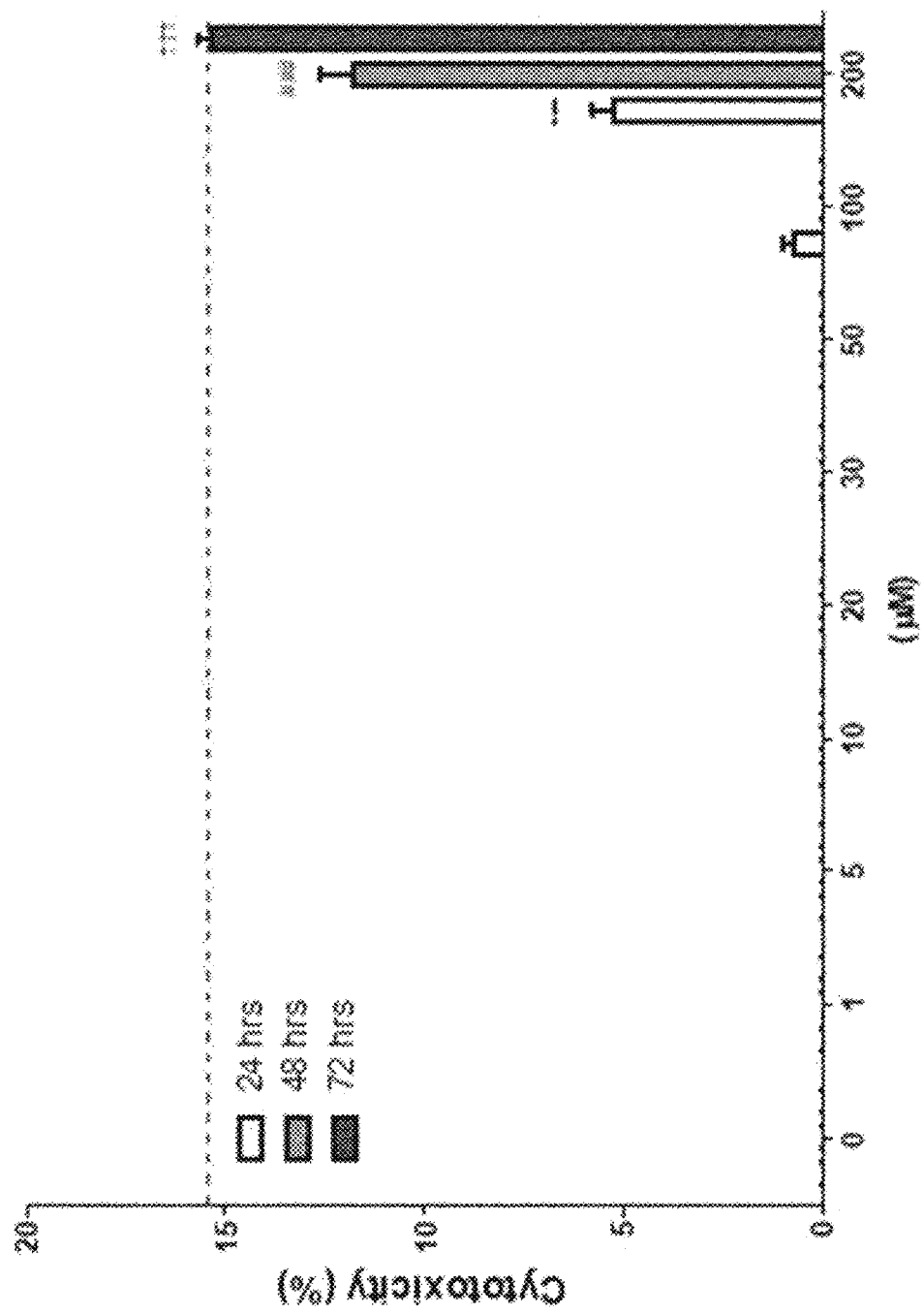

In FIG. 3A, cytotoxicity started to occur at a concentration of approximately M of ATRA. The culture for 24 hours at a concentration of 200 μM of ATRA exhibited the cytotoxicity of approximately 55%. On the contrary, in FIG. 3B, cytotoxicity started to occur at a concentration of approximately 100 μM of the compound MMB-11903B according to the present disclosure. The culture for 24 hours at a concentration of 200 μM of the compound MMB-11903B according to the present disclosure exhibited the cytotoxicity of approximately 5%. Thus, the compound MMB-11903B according to the present disclosure has significantly lower cytotoxicity compared to that of ATRA (for example, the culture for 24 hours at a concentration of 200 μM of the compound MMB-11903B according to the present disclosure exhibited cytotoxicity significantly lower by at least ten times than the culture for 24 hours at a concentration of 200 μM of ATRA exhibited).

4. Identification of Effects on Neurons
4-1) Changes in Morphology of Nerve Cells SH-SY5Y was grown in Minimum Essential Medium (MEM) medium supplemented with 10% Fetal bovine serum (FBS), 1% Antibiotic-Antimycotic (AA), and 2 mM L-Glutamine. For cell viability analysis, stabilized cells were planted in a 60 mm dish at a density of ×10⁵ cells/dish. The cells were attached to a 37° C., 5% $CO_2$ incubator and was allowed to be left so as to be stabilized for at least 14 hours. The next day, the growth medium was removed therefrom. 100 μL of Dulbecco's Modified Eagle Medium/Nutrient Mixture F-12 (DMEM/F-12=1:1) medium supplemented with 1% FBS, 1% AA, and 2 mM L-Glutamine for differentiation induction was diluted with each of the compound MMB-11903B acceding to the present disclosure synthesized in the Preparation example and DO3A of a following Chemical Formula as a compound for comparison to various concentrations (0, 5, 10, and 20 M). Then, the cells were incubated therein for 1, 3, and 5 days, and under at 37° C. and 5% $CO_2$ condition. Cell morphology was imaged with a Nikon inverted microscope (Nikon, ECLIPSE Ts2, Nikon Corporation, Tokyo, Japan). An image of a nerve cell line treated with each of DO3A and the compound MMB-11903B according to the present disclosure is shown in FIG. 4.

[Chemical Formula of DO3A]

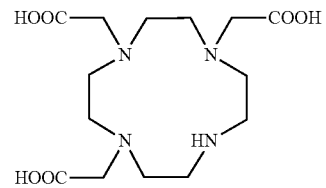

When the cells were treated with the compound MMB-11903B according to the present disclosure, change in cell morphology was observed at a low concentration of the compound. Differentiation into nerve cells was induced and the cell body became smaller, and a precursor of the axon and dendrite was elongated (neurite outgrowth) such that a length thereof became more than twice a length of the cell body. As the days has elapsed, the length of the neurite has expanded and formation of the neurite network became clearly observed. When the cells were treated with DO3A other than the compound MMB-11903B according to the present disclosure, the neurite elongation was not observed. However, apoptosis due to cytotoxicity was observed at 10 μM, 5 days and at 20 μM, and 3 days. DO3A does not have the ability to differentiate the neurite into nerve cells, but rather, causes cytotoxicity and thus is involved in nerve cell death. However, the compound MMB-11903B according to the present disclosure which has a backbone of DO3A has the ability to differentiate the neurite into nerve cells and has reduced cytotoxicity.

4-2) Test of Neurite Elongation Promoting Effect Using Immunofluorescence Staining SH-SY5Y was grown in Minimum Essential Medium (MEM) medium supplemented with 10% Fetal bovine serum (FBS), 1% Antibiotic-Antimycotic (AA), and 2 mM L-Glutamine. For cell viability analysis, stabilized cells were planted in a 60 mm dish at a density of ×10⁵ cells/dish. The cells were attached to a 37° C., 5% $CO_2$ incubator and was allowed to be left so as to be stabilized for at least 14 hours. The next day, the growth medium was removed therefrom. Dulbecco's Modified Eagle Medium/Nutrient Mixture F-12 (DMEM/F-12=1:1) medium supplemented with 1% FBS, 1% AA, and 2 mM L-Glutamine for differentiation induction was diluted with each of the compound MMB-11903B acceding to the present disclosure synthesized in the Preparation example and DO3A of the above Chemical Formula as a compound for comparison to a concentration 10 μM. Then, the cells were incubated therein for 1, 3, and 5 days, and under at 37° C. and 5% C02 condition. The cells were harvested and were washed with DPBS, and fixed with 10% Neutral Buffered Formalin for 10 minutes, washed 3 times with Tris-buffered saline (TBS), and then a reaction thereof was carried out for 15 minutes in 0.3% Triton X-100 (in TBS). The cells were washed three times in TBS, and a solution of 5% Bovine serum albumin (BSA) and Normal Goat Serum (NGS) in TBS was added thereto and a reaction thereof was carried out at 4° C. for 24 hours. Differentiation into the nerve cells and formation of the neurite were identified using j-III tubulin primary antibody as a neuron specific marker and doublecortin primary antibody as a newborn immature neuron marker. Reaction with the primary antibody occurred at 4° C. for 24 hours, the cells were washed 3 times in TBS and the secondary antibody reacted with Alexa Fluor®488 fluorescent (green) and Alexa Fluor®555 fluorescent (red) at room temperature for 1 hour. The cells were washed three times with TBS, and were mounted (VECTASHIELD® Mounting Medium with DAPI; Vector Laboratories, Burlingame, CA, USA), and images were acquired with a fluorescence microscope. The image thus obtained is shown in FIG. 5A. As may be identified in FIG. 5A, when the cells were treated with the compound MMB-11903B according to the present disclosure, neurite elongation and neurite network formation became observed clearly, whereas when the cells were treated with DO3A, neurite elongation was not observed.

The length of the elongated neurite was measured using the ImageJ program. Only a length of the neurite which was more than twice the length of the cell body, was measured. The calculated values were graphed using the GraphPad Prism application. The corresponding graph is shown in FIG. 5B. The statistical significance of the obtained values was identified via one-way ANOVA with Dunnett's multiple comparison test. $*p<0.5$, $***p<0.01$ vs. control, $\#\#p<0.1$, $\#\#\#p<0.01$ vs. DO3A indicate presence of statistical significance. Based on a result of measuring the length of neurites after fluorescent staining using a neuronal marker, it was identified that treatment with DO3A which corresponds to the backbone of MMB-11903B did not achieve the neurite elongation as in the control. Compared to the control and the DO3A treated group, treatment with the compound MMB-11903B according to the present disclosure induced the neurite elongation of the neuron such that the neurite elongation had an average increase of 1.7 times on the 1st day, an average increase of 2.6 times on the 3rd day, and an average increase of 2.5 times on the 5th day.

4-3) Test of Effect of Neurite Elongation and New Neuron Generation and Growth Using Immunofluorescence Staining In addition, according to the same method as the above method, but using not DO3A but ATRA as the comparative compound, differentiation into the nerve cell was observed based on immunofluorescence staining. The images obtained by fluorescence microscopy are shown in FIG. 6A.

The color histogram was measured using the ImageJ program. The calculated values were graphed using the GraphPad Prism application. The graph is shown in FIG. 6B. Compared to treatment with each of the control (untreated group) and a ATRA-treated group as a positive control, treatment with the compound MMB-11903B according to the present disclosure increased the differentiation and expression of neurons on day 3, and maintained high expression level until day 5. It was identified that treatment with each of the control (untreated group) and the ATRA-treated group as a positive control induced a low expression level of new neurons, while treatment with the compound MMB-11903B according to the present disclosure increased significantly the expression of new neurons on day 3. The statistical significance of the obtained values was identified via one-way ANOVA with Dunnett's multiple comparison test. $*p<0.5$, $***p<0.01$ vs. control, $\#p<0.5$, $\#\#p<0.1$, $\#\#\#p<0.01$ vs. ATRA indicate presence of statistical significance.

4-4) Test of Cell Proliferation Effect Using Immunofluorescence Staining

The number of cells which were positive relative to Ki-67 as a marker for neuronal proliferation was analyzed. The number of the positive cells was automatically obtained using the ImageJ program. The photograph obtained with a fluorescence microscope is shown in FIG. 7A.

Ki-67 positive cells (%)=(ki-67 positive cell number/ DAPI positive cell number)× 100 [Calculation equation of Ki-67 positive cell number]

The calculated values were graphed using the GraphPad Prism application. The corresponding graph is shown in FIG. 7B. On the 1st day of exposure, the group treated with each of the compound MMB-11903B of the present disclosure and DO3A had cell proliferation approximately two times larger than the control (untreated group) had. A group treated with ATRA did not exhibit a significant difference from that of the control. On the third day of exposure, all groups except for the ATRA-treated group exhibited neuronal proliferation. The group treated with the compound MMB-11903B according to the present disclosure exhibited a high neuronal proliferation until the 5th day. It was identified that the compound MMB-11903B according to the present disclosure promotes differentiation of the neurite into the nerve cells and also induces proliferation of new nerve cells. The statistical significance of the obtained values was identified via one-way ANOVA with Dunnett's multiple comparison test. $*p<0.5$, $p<0.1$, $*p<0.01$ vs. control, $\#p<0.5$, $\#\#p<0.1$ vs. DO3A, $†p<0.5$, $†††p<0.01$ vs. ATRA indicate statistical significance.

It may be identified from the above-mentioned Examples 4-1 to 4-4 that the compound MMB-11903B according to the present disclosure induces and maintains the proliferation of neurons in the nerve cell line more significantly, compared to DO3A or ATRA as controls, and at the same time, the compound MMB-11903B according to the present disclosure induces the generation and elongation of neurites to promote differentiation thereof into neurons.

Although the present disclosure has been described above with reference to the preferred examples of the present disclosure, those skilled in the art may variously modify the present disclosure without departing from the spirit and scope of the present disclosure as described in the claims below.

What is claimed is:

1. A compound represented by a following Chemical Formula 1:

[Chemical Formula 1]

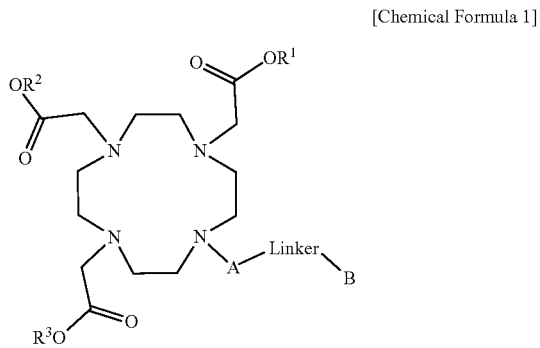

wherein in the Chemical Formula 1, each of $R_1$ to $R_3$ independently represents hydrogen, linear or branched (C1-C10)alkyl, or an electron pair to form any bond, A represents *—$(CH_2)_n$-$A^1$-*, n represents any integer from 0 to 5, $A^1$ represents *—COO—*, *—CO—*, *—$NR^4$—*, *—$CH_2$—*, *—CONH—*, or *—O—*, Linker represents *-$L^1$-NHCO-$L^2$-*, *-$L^1$-O—R—O-$L^2$-*, *-$L^1$-$CH_2$-$L^2$-*, *-$L^1$-$NR_5$-$L^2$-*, or *-$L^1$-COO-$L^2$-*, $L^1$ represents linear or branched (C1-C30)alkyl, $L^2$ represents a single bond or linear or branched (C1-C30)alkyl, R represents linear or branched (C1-C20)alkyl, each of $R^4$ and $R^5$ independently represents hydrogen or linear or branched (C1-C10)alkyl, and B represents a moiety derived from retinoic acid.

2. The compound according to claim 1, wherein B is represented by a following Chemical Formula 2a, 2b, or 2c:

[Chemical Formula 2A]

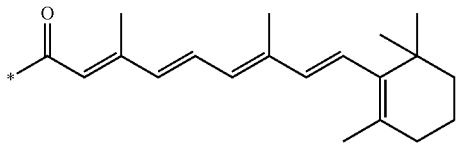

[Chemical Formula 2B]

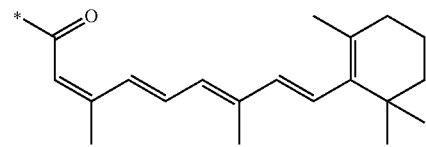

[Chemical Formula 2c]

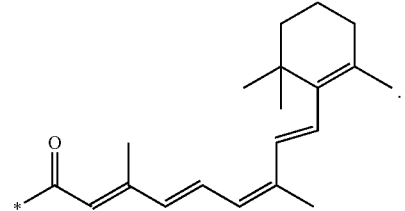

3. The compound according to claim 2, wherein B is represented by the Chemical Formula 2a.

4. The compound according to claim 1, wherein each of $R^1$ to $R^3$ represents hydrogen or an electron pair to form any bond.

5. The compound according to claim 1, wherein n represents any integer from 1 to 5, and $A^1$ represents *—CONH—*.

6. The compound according to claim 1, wherein Linker represents *-$L^1$-$NR_5$-$L^2$-*, and $R^5$ is hydrogen.

7. The compound according to claim 1, wherein $L^1$ represents linear or branched (C1-C10)alkyl, and $L^2$ represents a single bond.

* * * * *